United States Patent
Lake et al.

(10) Patent No.: US 12,004,929 B2
(45) Date of Patent: Jun. 11, 2024

(54) TAMPON PRODUCT INCLUDING APPLICATOR HAVING COMPONENTS MOLDED OF PULP-BASED COMPOSITE

(71) Applicant: The Procter & Gamble Company, Cincinnati, OH (US)

(72) Inventors: David Daniel Lake, Cincinnati, OH (US); Ryo Minoguchi, Cincinnati, OH (US); Khalid Qureshi, Mason, OH (US); Paul Thomas Weisman, Cincinnati, OH (US); Keisuke Matsuzaka, Tottori (JP); Tetsu Nishikawa, Kyoto (JP)

(73) Assignee: The Procter & Gamble Company, Cincinnati, OH (US)

( * ) Notice: Subject to any disclaimer, the term of this patent is extended or adjusted under 35 U.S.C. 154(b) by 122 days.

(21) Appl. No.: 17/700,563

(22) Filed: Mar. 22, 2022

(65) Prior Publication Data
US 2022/0296434 A1 Sep. 22, 2022

Related U.S. Application Data

(60) Provisional application No. 63/163,985, filed on Mar. 22, 2021.

(51) Int. Cl.
*A61F 13/26* (2006.01)
*A61F 13/20* (2006.01)

(52) U.S. Cl.
CPC ........ *A61F 13/266* (2013.01); *A61F 13/2082* (2013.01)

(58) Field of Classification Search
CPC .............. A61F 13/25–28; A61F 13/266; A61F 13/2082
See application file for complete search history.

(56) References Cited

U.S. PATENT DOCUMENTS

| | | | | |
|---|---|---|---|---|
| 3,581,744 | A * | 6/1971 | Voss | A61F 13/2085 604/14 |
| 5,496,874 | A * | 3/1996 | Faass | A61F 13/26 524/386 |
| 6,508,780 | B1 * | 1/2003 | Edgett | A61F 13/26 604/15 |
| 7,048,975 | B1 * | 5/2006 | Tojo | B65D 1/0215 428/34.3 |
| 2003/0040695 | A1 * | 2/2003 | Zhao | A61F 13/26 604/15 |

(Continued)

FOREIGN PATENT DOCUMENTS

| | | | |
|---|---|---|---|
| EP | 2511346 A1 | 10/2012 | |
| JP | 2019183320 A | * 10/2019 | ............... D21J 3/00 |

OTHER PUBLICATIONS

PCT Search Report and Written Opinion for PCT/US2022/071247 dated Jul. 4, 2022, 13 pages.

*Primary Examiner* — Susan S Su
(74) *Attorney, Agent, or Firm* — Sarah M. DeCristofaro; William E. Gallagher

(57) ABSTRACT

A tampon applicator assembly is disclosed. The applicator assembly may include a barrel portion, a grip portion and an ejection plunger configured to slide coaxially within one or both the barrel portion and the grip portion. One or more of the barrel portion, grip portion and ejection plunger may be molded from a molding composite comprising cellulose fibers.

20 Claims, 5 Drawing Sheets

(56) References Cited

U.S. PATENT DOCUMENTS

| | | |
|---|---|---|
| 2003/0105421 A1* | 6/2003 | Jarmon ............. A61F 13/15211 |
| | | 604/11 |
| 2010/0016780 A1 | 1/2010 | Vandenbogart et al. |
| 2012/0035526 A1 | 2/2012 | Colin et al. |
| 2013/0281912 A1* | 10/2013 | Mikhail ............ A61F 13/15252 |
| | | 264/301 |
| 2014/0263037 A1* | 9/2014 | Schouweiler .......... B01D 39/18 |
| | | 210/504 |
| 2019/0021914 A1 | 1/2019 | Demarco et al. |
| 2020/0155363 A1 | 5/2020 | Dougherty et al. |
| 2020/0216624 A1 | 7/2020 | Hamilton et al. |

* cited by examiner

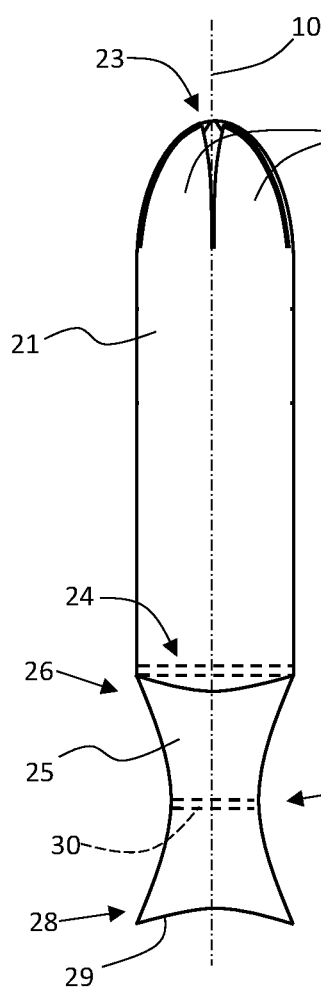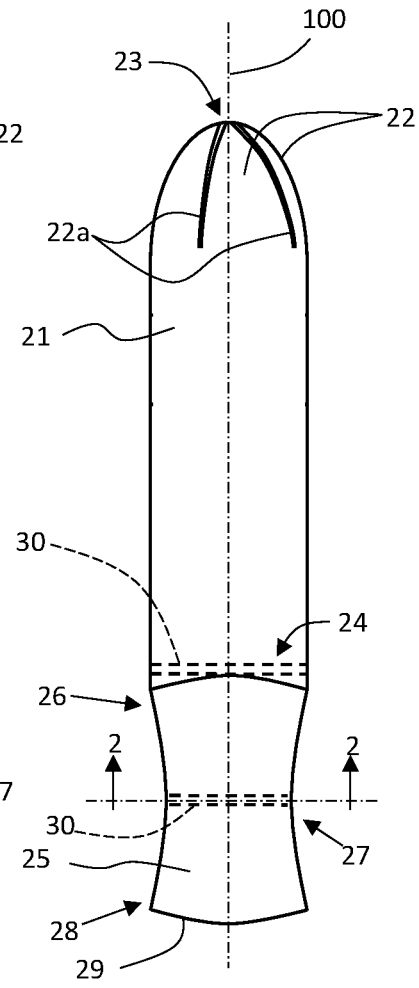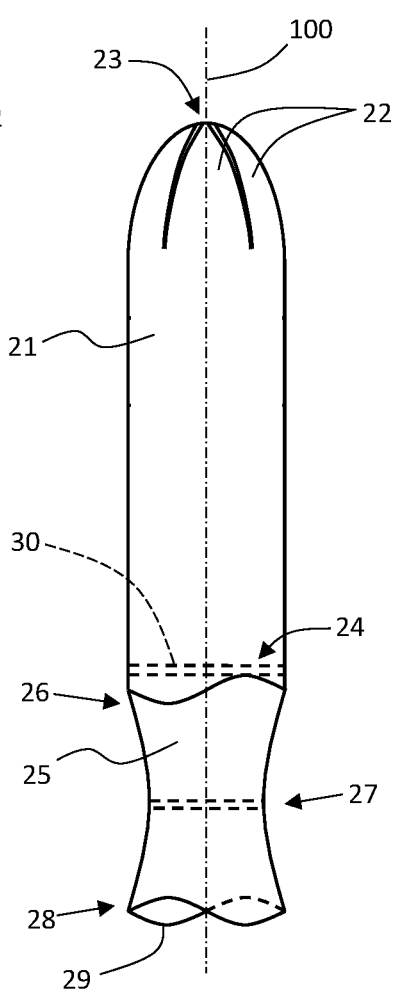
FIG. 1A    FIG. 1B    FIG. 1C
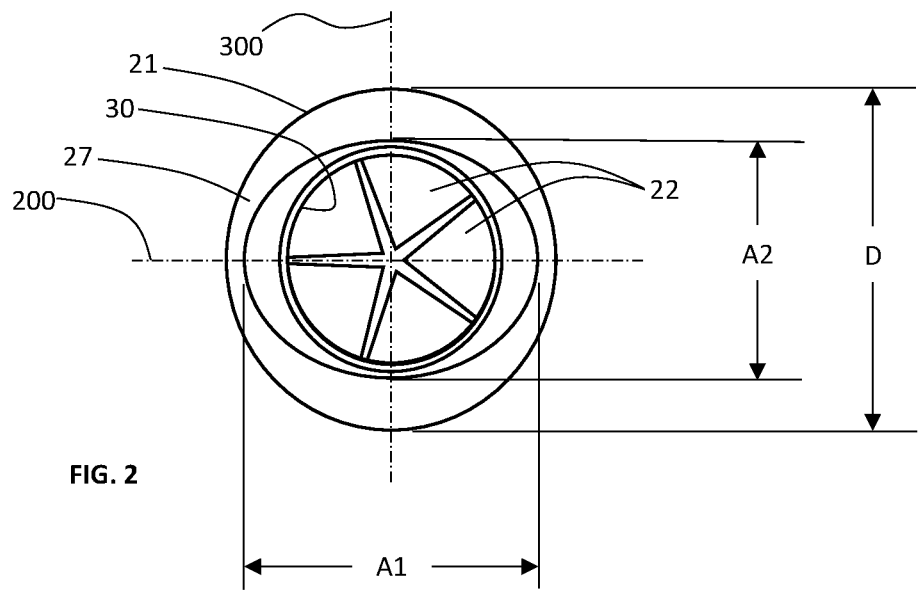
FIG. 2

TAMPON PRODUCT INCLUDING APPLICATOR HAVING COMPONENTS MOLDED OF PULP-BASED COMPOSITE

CROSS REFERENCE TO RELATED APPLICATION

To the fullest extent appropriate this application claims the benefit of U.S. Provisional Application No. 63/163,985, filed Mar. 22, 2021, the substance of which is incorporated herein by reference.

BACKGROUND

Tampons have been used by women for many years to contain and absorb menstrual fluid during menstruation, to avoid soiling undergarments, outer clothing, bedding, etc. The typical currently marketed tampon is formed of an absorbent structure that may include absorbent material(s) such as rayon and cotton. The structure is typically formed and compressed into a cylindrical shape about the size of a small finger, having a forward/insertion end and a rearward end, and configured to be easily inserted into suitable position in the vaginal cavity, and then to expand therewithin as it is contacted by and absorbs menstrual fluid, and swells with the absorbed fluid. Typically, a tampon will include a securely attached withdrawal cord extending from its rearward end, of a length sufficient to extend down the vaginal canal and outside the vagina during and after insertion of the tampon into suitable position. After a desired length of time following insertion the user may pull the cord to withdraw and remove the tampon.

Some users prefer tampons that are unaccompanied by applicators, preferring to use a finger to push the tampon to a suitable position within the vaginal cavity.

Other users, however, prefer a tampon that is provided with an applicator assembly that houses and protects the new tampon prior to use, and facilitates insertion without the need to insert a finger into the vaginal canal. The typical applicator assembly includes a hollow barrel portion, often of a substantially cylindrical shape and having a forward end and a rearward end, within which the new tampon is contained. The applicator assembly also typically includes an ejection plunger that is disposed in contact with the rearward end of the tampon inside the barrel portion, and extends rearwardly from the rearward end of the barrel portion, and is configured to slide coaxially into the rearward end of the barrel portion and thereby provide a mechanism by which the user can push the tampon out the forward end of the barrel portion. The barrel portion may be joined, at a rearward extent thereof, to a grip portion, having a contoured shape and/or surface texturing that differ from more forward portions of the barrel portion, and thereby provide for the user a tactile signal of orientation of the assembly and location of the rearward end, and enhanced slip resistance for gripping purposes. The forward end of the barrel portion may be rounded or tapered to a gently rounded but openable tip to facilitate insertion. An openable configuration may be formed at the forward end, of a group of radially-arranged flexible petals that are rounded and curved inwardly at their distal/forwardmost ends toward the longitudinal axis of the applicator assembly, to close off the forward end and contain and protect the new tampon contained within, but flex radially outwardly under contact and forward pressure by the tampon as it advances forwardly within the applicator, to open and allow the tampon to be urged forward and out of the forward end of the barrel portion when the ejection plunger is pushed by the user. Applicator assemblies and their component parts may be formed of various materials and have a variety of design features, to enhance the user experience and facilitate cost-effective manufacture.

In some currently-marketed examples, one or more of the barrel portion, grip portion and ejection plunger may be molded (e.g., via injection molding) from a plastic (such as polyethylene (PE)). This material and method of production provide advantages in that an applicator barrel may be provided with a non-absorbent, smooth and glossy, low-friction surface that provides for easy and comfortable insertion. Plastic injection molding also allows for any number of variations in formation of shapes and surface texture features, for purposes of providing, e.g., a differentiated grip portion, and/or formation of internal functional features to the ejection mechanism.

In recent years, economic and environmental concerns, and related regulatory pressures, have begun to mount, to some extent against use of materials derived from petroleum (including plastics such as PE), and to some extent against use of materials that are not dispersible in water and/or rapidly biodegradable in, e.g., landfills (including plastics such as PE). More specific to tampons and applicators, an applicator assembly (or components thereof) formed of plastic (such as or having similarities to PE) do not break up or disperse in water, may clog sewage pipes, may not easily be processed by a sewage treatment plant, and are not rapidly biodegradable.

In other currently-marketed examples of tampon products, one or more of the barrel portion, grip portion and ejection plunger may be formed of paperboard, whose primary constituent is cellulose pulp. While this material addresses some of the concerns identified above in that it is generally biodegradable, currently-marketed paperboard applicators typically include binders and/or surface coatings derived from petroleum. Further, currently known technologies do not facilitate providing paperboard applicators with detailed attractive and/or functional features commonly available with molded plastic applicators.

Accordingly, any improvements to features that address any of the issues described above may provide the manufacturer/seller of tampons with applicator assemblies a competitive advantage.

BRIEF DESCRIPTION OF THE DRAWINGS

FIG. 1A is a longitudinal side view of the barrel and grip portions of an applicator assembly in a first rotational orientation about its longitudinal axis.

FIG. 1B is a longitudinal side view of the barrel and grip portions shown in FIG. 1A, in a second rotational orientation about its longitudinal axis 90 degrees from the first rotational orientation.

FIG. 1C depicts is a longitudinal side view of the barrel and grip portions shown in FIG. 1A, in a third rotational orientation about its longitudinal axis 45 degrees from the first rotational orientation.

FIG. 2 is a lateral cross section of the barrel and grip portions as shown in FIG. 1B, taken through line 2-2 in FIG. 1B.

DEFINITIONS

Figure 3A:
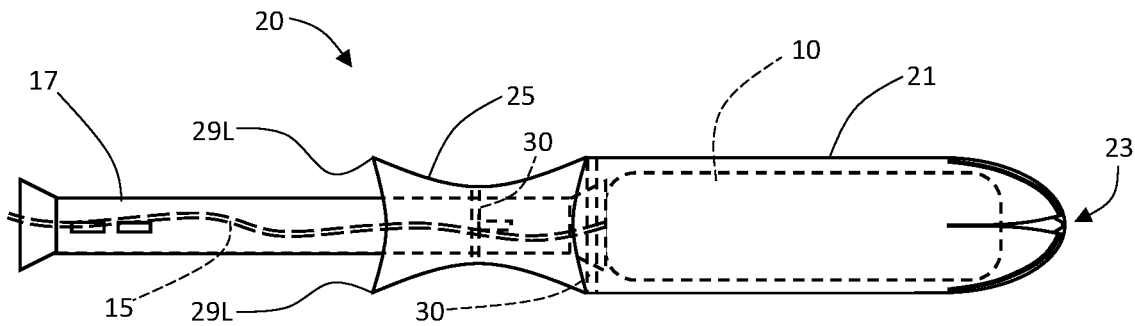
FIG. 3A is a longitudinal side view of an applicator assembly containing a tampon, in a first rotational orientation about its longitudinal axis, prior to ejection of the tampon.
Figure 3B:
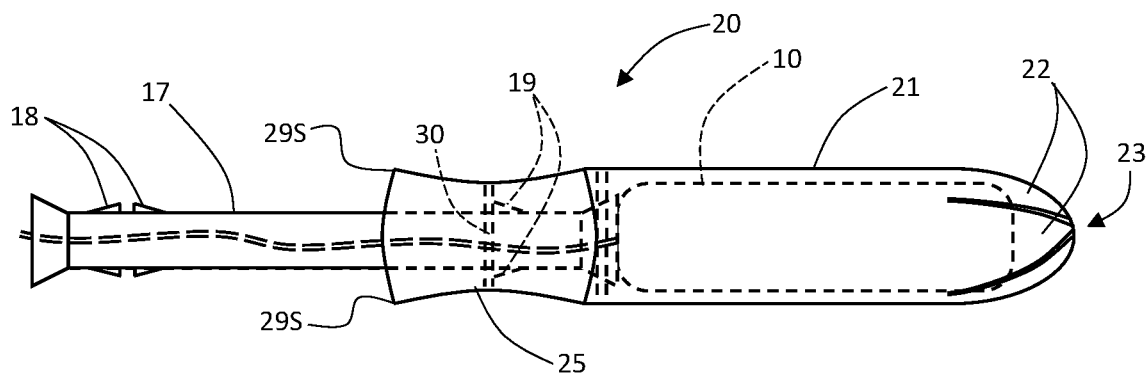
FIG. 3B is a longitudinal side view of an applicator assembly containing a tampon, in a second rotational orientation about its longitudinal axis 90 degrees from the first rotation, prior to ejection of the tampon.
Figure 4A:
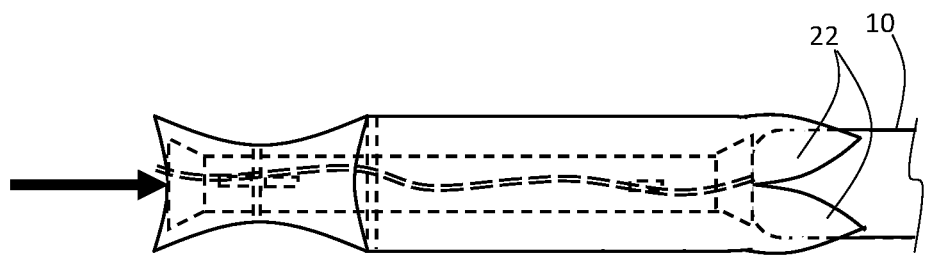
FIG. 4A is a longitudinal side view of an applicator assembly containing a tampon, in a first rotational orientation about its longitudinal axis, with the plunger portion pushed into the barrel portion and near completion of ejection of the tampon.
Figure 4B:
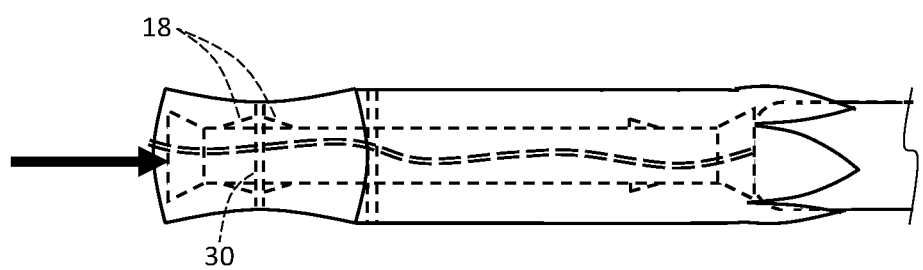
FIG. 4B is a longitudinal side view of an applicator assembly containing a tampon, in a second rotational orientation about its longitudinal axis 90 degrees from the first rotation, with the plunger portion pushed into the barrel portion and near completion of ejection of the tampon.

As used herein "applicator assembly" refers to a device or implement configured to house, and facilitate the insertion and placement of, a tampon, pessary, menstrual cup or other device into a user's vaginal cavity. An applicator assembly is configured to be inserted into a user's vaginal cavity. Non-limiting specific examples of such include any known applicator assembly that may be used for insertion of a tampon, such as telescoping tube and plunger assemblies.

"Substantially parallel," with respect to two coplanar lines of direction, describes lines of direction that are precisely parallel (never intersect), and coplanar lines of direction that intersect and thereby deviate from precisely parallel, by no more than 10 degrees.

"Substantially perpendicular," with respect to two coplanar lines of direction, describes lines of direction that are precisely perpendicular (intersect at an angle of 90 degrees), and coplanar lines of direction that deviate from precisely perpendicular by no more than 10 degrees (i.e., intersect at an angle from 80 degrees to 100 degrees).

As used herein, "substantially cylindrical" refers to and includes the outer shape of a cylinder, but also includes shapes such as slightly oblate or slightly flattened cylinders, slightly curved cylinders, and other tubular shapes which have diameters and/or cross-sectional areas that vary slightly along their lengths, wherein minor deviation from a precise cylindrical shape does not compromise product manufacturability, function or utility.

The "longitudinal axis" of a tampon, or of a barrel portion or other component of an applicator assembly, is the line along the normal direction of insertion of the tampon and applicator by a user, through the geometric center of a lateral cross section profile of the applicator assembly component, where the cross section lies along a plane perpendicular to the normal primary direction of insertion. The longitudinal axis of an example of the barrel portion of an applicator assembly is illustrated in FIGS. 1A-1C.

"Lateral" with respect to a tampon or applicator assembly refers to a direction perpendicular to its longitudinal axis. "Width" refers to a dimension measured along a direction perpendicular to the longitudinal axis.

"Longitudinal" with respect to a tampon or applicator assembly refers to a direction parallel to its longitudinal axis.

"Length" refers to a dimension measured along a direction parallel to the longitudinal axis.

"Axial" movement of an element means movement along the longitudinal axis of an element. An "axial" direction is substantially parallel to the longitudinal direction.

"Coaxial" refers to the movement of an ejection plunger within a barrel portion of an applicator assembly, whereby the plunger moves within the barrel portion and substantially along and/or parallel to longitudinal axis of the barrel portion.

"Vaginal cavity" refers to the internal body cavity of a human female, extending between the introitus of the vagina (sometimes referred to as the opening or sphincter of the vagina) and the cervix.

Tampon Construction

Typically, a tampon is manufactured of one or more absorbent materials, which have been assembled, cut, shaped and compressed in one or both of the lateral direction and the axial direction, in order to provide a body of a size and stability of form when dry to allow for neat insertion into a user's vaginal cavity. Components, assembly methods, and precompression configurations and shapes may vary among manufacturers and/or manufacturing processes. A new tampon has a forward (insertion) end and a rearward (withdrawal) end. When housed in an applicator assembly, the forward end is proximate the forward (insertion) end of the barrel portion of the applicator assembly, proximate the petals (when included) of the barrel portion. Tampons intended for placement in the vaginal cavity to absorb menstrual fluid typically have a substantially cylindrical compressed shape prior to application. Preferably, a new tampon will substantially retain its compressed shape and size as long as it is kept dry, prior to insertion and use. The pre-application shape and size need not persist following insertion and during use. Tampons typically expand in size and change shape in varying ways during use, as they are contacted by and absorb fluid.

Tampons also may be manufactured and formed to have other shapes and forms, as described in, for example, U.S. Pat. Nos. 6,824,536; 6,932,805; 8,597,267; 8,684,987; 8,216,202; 6,953,456; 6,554,814; 7,549,982; 6,939,340, and 8,029,485.

The tampon may be a non-layered, uniform structure, or it may be a laminar structure comprised of integral or discrete layers, or the tampon may have a folded structure, or it may be rolled, or any other suitable structure known in the art. Generally, it may be preferred that the tampon have a certain minimal rigidity and structural shape integrity when new and dry, to facilitate ejection from an applicator assembly and/or insertion, by pushing on the rearward end.

The tampon may be constructed from a variety of liquid-absorbing materials commonly used in absorbent articles, such as, for example, rayon, cotton, or comminuted wood pulp (which is generally referred to as airfelt). Examples of other suitable absorbent materials include creped cellulose wadding; formations including meltblown filaments spun from polymeric resin, including coformed formations; chemically stiffened, modified or cross-linked cellulosic fibers; synthetic fibers such as crimped polyester fibers; peat moss; absorbent foams; tissue including tissue wraps and tissue laminates; or any other suitably absorbent material or combination or blend of absorbent materials. Preferred absorbent materials include cotton and rayon (including tri-lobal and conventional rayon fibers, and needle punched rayon). Suitable types of rayon may include GALAXY rayon (a tri-lobal rayon fiber structure) available as from Kelheim Fibres GmbH of Kelheim, Germany, and TENCEL rayon (a round fiber rayon) available from Lenzing AG, Lenzing, Austria. Suitable cotton material includes, long fiber cotton, short fiber cotton, cotton linters, T-fiber cotton, card strips, and comber cotton. Additionally, superabsorbent materials, such as superabsorbent polymers or absorbent gelling materials in particle or fiber form may be incorporated into the tampon.

The absorbent material(s) of the tampon may be surrounded by an overwrap. The overwrap is preferably a liquid permeable material. Such materials may include knitted, woven or nonwoven fabrics of rayon, cotton, fibers spun from polymeric resins, including bicomponent fibers, or any other suitable natural or synthetic fibers known in the art. Rayon, polyethylene, polypropylene and blends of these are particularly suited for use as overwrap material. Synthetic fibers may include fibers spun or formed of polyester, polyolefin, nylon, polypropylene, polyethylene, polyacrylic, cellulose acetate, or combinations of these, such as bicomponent fibers. Natural fibers or semi-synthetic fibers may include fibers of cotton or rayon. In general, cotton and/or rayon fibers may be preferred for inclusion because they provide ready absorption and fluid wicking. Synthetic (polymer-based) fibers may also be preferred for inclusion for their surface characteristics and properties to balance the capillarity of more absorbent materials included, and enable the tampon to more readily slip against moist tissue, resulting in easier and more comfortable tampon insertion and removal. The overwrap may be adapted or formed to extend rearwardly beyond the rearward end of the assembly of absorbent material(s) to form a skirt portion, as described in U.S. Pat. No. 6,840,927, for example. The overwrap may be configured to extend from about 2 mm to about 30 mm beyond the rearward end of the assembly of absorbent material(s).

The tampon may include a withdrawal cord, which may be attached to or along any portion of the tampon. This may be any type of withdrawal cord known in the art, for example a generally braided (or twisted) withdrawal cord. A conventional type of withdrawal cord (in terms of thickness, material composition, etc.) may be periodically braided with a thicker slub of fibrous material, which acts as a wicking member, to form a structure to be connected to the remaining of the tampon. In such an embodiment, the portion of the cord, which will act as the withdrawal cord, may be treated to make it non-absorbent or even hydrophobic. It may also be a withdrawal cord as described in commonly assigned and co-pending U.S. application Ser. No. 09/309,467.

The tampon may contain any additional functional ingredients, such as antimicrobial agents, lubricants, antioxidants, pH modifiers, etc., as known in the art.

The tampon may also include a wicking member or secondary absorbent structure such as, for example, described and/or identified in US2020/0188186.

It may be preferred in some circumstances that the tampon may comprise a chevron-shaped pad, which also may be of a laminar construction, prior to compression into a substantially cylindrical form. This pad may be formed to have a lateral width and a longitudinal length wherein the width is greater than the length. The pad may include at least three layers of absorbent material, including an uppermost layer, a lowermost layer, and at least one intermediate layer positioned between the uppermost layer and lowermost layer. Each of the uppermost layer and the lowermost layer may be formed primarily of rayon, and the at least one intermediate layer may be formed primarily of cotton, rayon, or a blend thereof.

Applicator Assembly

A tampon may be provided new within an applicator assembly, configured to contain and protect the tampon until use, and then to facilitate insertion of the tampon without the need to insert a finger into the vaginal cavity to push the tampon into suitable position. An applicator assembly having a barrel and plunger arrangement may be preferred. Barrel and plunger portions may be formed of molded polymer resin, paper, molded cellulose pulp-based composites, or other suitable material, or a combination thereof. It may be desirable in some circumstances that one or more components of the assembly be translucent or transparent to allow the user to view the tampon or a feature thereof within the assembly, for example, to determine whether the assembly contains a tampon (i.e., has not been used), or to make features of the tampon visible from outside the applicator. In some circumstances it may be desired that the material(s) forming the applicator be tinted or pigmented to impart a non-white color for esthetic purposes and/or to reduce visibility of menstrual fluid that may be deposited thereon following use. In some circumstances it may be desired that one or more components of the applicator assembly be substantially opacified, or opacified and tinted or pigmented, or imprinted with ink on outer surfaces to impart coloration or a decorative design.

The applicator assembly may be corrugated as described in U.S. Pat. No. 7,066,870. The applicator assembly may be provided with a grip portion as described in U.S. Pat. Nos. 8,303,558; 7,081,110; 8,449,491, or U.S. Pat. No. 8,075,512. The applicator assembly may be provided with an absorbency indicator as described in U.S. Pat. No. 7,166,101.

The applicator assembly may be provided with a cap and/or insertion tip portion that allows for a smooth and safe insertion. A rupturable cap may be provided as described in U.S. Pat. No. 6,610,025, that will protect the tampon from contamination prior to use, but will rupture and allow the tampon to be pushed forward and out of the applicator assembly when the user desires to do so. The cap or a forward end portion of the assembly may be formed of or include flexible or movable petals as described in U.S. Pat. No. 6,652,477.

Referring now to FIGS. 1A-1C, 2, 3A, 3B, 4A and 4B, an applicator assembly 20 may include a barrel portion 21, a grip portion 25 and an ejection plunger 17.

Barrel portion 21 may include an approximately or substantially tubular and hollow section which may also include a substantially cylindrical outer shape, having a forward end 23 and a rearward extent 24, and may be sized and proportioned to snugly contain a compressed tampon 10 (see FIGS. 3A, 3B), while serving as a vehicle for facilitating comfortable delivery of the tampon to a suitable location within the vaginal cavity. In some examples barrel portion 21 may have a lateral cross section profile that is substantially circular; in other examples it may have a lateral cross section outer profile that is oval-shaped, ovoid-shaped, stadium-shaped or elliptical. Barrel portion 21 may have a forward/insertion end portion formed by a group of radially-arranged, flexible petals 22 defined by clefts 22*a* therebetween as suggested in the figures (clefts 22*a* are identified, in one example, FIG. 1B). Petals 22 may be shaped and rounded radially inwardly as they approach the forward end 23, as suggested in the figures, to neatly form a smoothly tapering, rounded forward/insertion end portion/tip to facilitate easy and comfortable insertion. In some examples petals 22 may be integral extensions of the barrel portion 21, which are molded, heat-formed or otherwise shaped with a rounded taper as suggested in the figures.

Grip portion 25 may have a forward portion 26, an intermediate portion 27, a rearward portion 28 and a rearward edge 29. In some examples grip portion 25 may include a circumferential flange or collar portion laterally/radially extending from the surface, as described in U.S. Pat. No. 9,283,122 (not specifically shown in the present drawings). As suggested in FIGS. 1A-1C, grip portion 25 may have a shape that transitions from a first larger lateral dimension where it joins barrel portion 21, to a smaller lateral dimension at intermediate portion 27, and flaring to a second larger lateral dimension at rearward portion 28. This provides a tactilely-perceivable portion of the applicator assembly at which the user can intuitively, comfortably and ergonomically identify and grip the applicator assembly with opposing fingers, to manipulate the applicator assembly to insert a tampon. In some examples the grip portion 25 may be provided or formed with a rubberized surface, or a surface having increased tack or increased coefficient of friction with human skin relative the barrel portion surface, or surface finish, textural features, or surface topographic features (which may include esthetic/decorative elements) or any combination of these features (not specifically shown), for gripping slip resistance. When such features are provided on the grip portion 25 but are absent on a majority of the outer surface area of the barrel portion 21, such features may provide further tactile and/or visible means of identification of the grip portion for the user.

Texture or topographic features on the surface may be both functional, for gripping slip resistance, and decorative, for esthetic appeal. Grip portion 25 may be integrally molded or formed with barrel portion 21, or may be separately formed and then joined to barrel portion 21 via fusion/welding, thermal bonding, adhesive bonding, chemical bonding or other suitable bonding mechanism (such as, for example, that described below, for bonding of components molded of cellulose pulp-based composite), or may be joined to the barrel portion via cooperating physical/mechanical features. For purposes of efficient manufacture and structural integrity, in some circumstances it may be preferred that grip portion 25 be integrally formed with/joined to barrel portion 21. Barrel portion 21 may be formed of any suitable material having, or imparted with, suitable surface properties that provide for substantial non-absorption of body fluids (i.e., during the brief time of insertion and withdrawal in normal use) and low friction against moist tissue, to provide for ease and comfort of insertion and withdrawal. In some examples barrel portion 21 may be formed of a cardboard or paperboard tube, or a cellulose pulp-based composite as described below, having an outer coating (e.g., including a wax or polymer) to provide for non-absorption of fluid and low friction. In other examples barrel portion 21 may be formed of a polymeric resin. In more particular examples barrel portion 21 may be formed of injection-molded polymeric resin predominately constituted by polyethylene, which may provide suitable non-absorption and low surface friction characteristics. In other examples barrel portion 21 may be formed of a cellulose pulp-based composite, and imparted with suitable non-absorption and low surface friction characteristics. In particular examples barrel portion 21 and grip portion 25 may be integrally injection molded together.

Preferably, the majority of the outside surface area of the barrel portion 21 is provided with a smooth and/or glossy surface finish, to provide for low friction with tissues during use. In contrast, the grip portion may be provided with a matte (or rougher) surface finish and/or any combination of the above-described features for enhancing gripping slip resistance.

To further enhance rapid visual and/or tactile identifiability of the grip portion, the grip portion and the barrel portion may be provided with visibly differing/contrasting colors; visibly differing levels of opacity/transparency/translucency; visibly/tactilely differing surface finishes, visibly/tactilely differing/contrasting surface texture features, tactilely differing/contrasting structural stiffness (e.g., grip portion 25 may be formed with thicker walls relative the barrel portion walls, resulting in a relatively stiffer grip portion structure that may be tactilely perceived), or any combination thereof. Additionally, or in combination, the respective barrel and grip portions 21, 25 may be formed of or include respectively differing component materials or formulations thereof, that impart any of the visibly and/or tactilely perceivable differences listed in the preceding sentence.

Referring to FIGS. 3A, 3B, 4A and 4B, an applicator assembly 20 may be provided with an ejection plunger 17, configured along with the barrel portion and grip portion to fit and slide coaxially within the barrel portion and grip portion. The ejection plunger 17 may be hollow and cylindrical. As such, in some examples, the ejection plunger can be hollow so as to provide a central axial space within which a withdrawal cord 15 attached to and extending rearward from tampon 10 may reside prior to use. In some examples, the ejection plunger 17 may have one or both ends flared as shown or otherwise formed to have relatively enlarged pushing surfaces, which contact the tampon 10 and the user's pushing finger, during application, respectively.

In some examples, the ejection plunger 17 may include two coaxially-arranged sub-portions (not shown) wherein one sub-portion may slide coaxially within the other in telescope fashion, as described and depicted in US 2015/0060317. Such a configuration for the ejection plunger may be included to provide the advantages described in the cited reference. In some examples the two sub-portions may be formed of a cardboard or paperboard tube, or molded from a cellulose pulp-based composite as described below, or combinations of them. The two sub-portions may be provided with respective visibly differing colors; respective visibly and/or tactilely differing surface finishes, respective visibly and/or tactilely differing surface textural features, respective tactilely differing structural stiffness or rigidity, or any combination thereof.

The barrel portion 21 and/or grip portion 25 may be provided with one or more internal plunger guides 30, to provide a relatively close internal tolerance between the ejection plunger 17 and the barrel and/or grip portions 21, 25, disposed at at least two differing longitudinal positions within the barrel portion and/or grip portion. Plunger guides 30 may be provided and suitably configured and sized to provide clearances that ensure that the plunger may effectively freely slide longitudinally therewithin, but be guided substantially linearly/coaxially through the gripping and barrel portions to enable smooth and efficient ejection of the tampon 10 from barrel portion 21 during application. The ejection plunger 17 may be provided with one or more retainer structures 19 that cooperate with internal features of the barrel portion and/or the grip portion (such as plunger guides 30) to prevent the plunger 17 from sliding out and away from the rear of the grip portion. The plunger 17 also may be provided with one or more latching/detent structures 18 that cooperate with internal features of the barrel portion and/or the grip portion (such as plunger guides 17) to latch the plunger 17 into a forward position following substantial ejection of the tampon 10, indicating that the applicator assembly has been used, and retaining the applicator (including the ejection plunger) in a more compact form for carrying and disposal following its use (as appears in FIGS. 4A and 4B).

Comparing FIGS. 3A and 3B and FIGS. 4A and 4B, it can be appreciated that flexible petals 22 can be formed and configured to flex about bases thereof at the barrel portion, radially outwardly from the longitudinal axis, spreading to create and/or enlarge an opening at the forward end of the applicator assembly, through which the tampon 10 can be ejected during application.

As may be appreciated from FIGS. 1A-1C and 2, grip portion 25 may have additional features that enhance its utility. Grip portion 25 may be configured to be visually and tactilely distinguishable from barrel portion 21 by a transition to a differing outer shape, size or geometry, at forward portion 26, the differing shape, size or geometry having one or more lateral dimensions that are smaller than a smallest lateral dimension of the barrel portion 21 proximate the forward portion 26. Barrel portion may include a substantially cylindrical portion having a circular lateral outer cross section profile having an outer diameter D. The transition may be gradual or abrupt. In the example depicted in the figures, in a first rotational orientation reflected in FIG. 1A, intermediate portion 27 may have its smallest lateral dimension, shown along minor axis 300 of its lateral cross section as dimension A2 in FIG. 2. In a second rotational orientation reflected in FIG. 1B (90 degrees from the first rotational orientation, rotated about longitudinal axis 100), intermediate portion 27 may have its largest lateral dimension, shown along major axis 200 of its lateral cross section as dimension A1 in FIG. 2. For example, a lateral cross section through the intermediate portion may have an outer profile that is non-circular. In various non-limiting examples, the lateral outer cross section profile may have, substantially, a rounded rectangle shape, an elliptical shape, an oval shape, an ovoid shape or a stadium shape. In some examples, the lateral outer cross section profile of the grip portion may have a lateral cross section that is non-circular at the intermediate portion 27 but transitions smoothly from non-circular to circular, moving from intermediate portion 27 to forward portion 26 wherein it joins a substantially cylindrical barrel portion 21. In some examples, the outer profile of the grip portion may have a lateral cross section that is non-circular through the intermediate portion 27 but transitions smoothly from non-circular to circular, moving from intermediate portion 27 to rearward portion 28 where it ends at rear edge 29. In some examples, the grip portion 25 may be formed with an outer shape that at least partially defines a hyperbolic paraboloid.

This difference in lateral dimensions between rotational orientations of the grip portion 25 may enhance its slip resistance and/or ergonomic feel. It also may serve to provide the user with a tactile indication of rotational orientation of the applicator assembly, which may be useful in examples in which the tampon within the barrel portion has directionality or differing shape or expansion features according to the tampon's rotational orientation about longitudinal axis 100.

In addition to the features described above, the applicator assembly may be provided with any of the features described in U.S. application Ser. No. 16/824,934. The applicator assembly together with a new tampon housed therein may be provided to the consumer within a wrapper (not shown). The wrapper may be formed of nonwoven web, paper, polymer film, any laminate combination thereof, or any other suitable materials, and may be imparted with any other suitable features such as, for example, those described in US2008/01186789.

Materials and Manufacturing Method

It has been found that cellulose pulp-based composites may be formulated, that are suitable for injection molding in conventional molds adapted for use to mold applicator assembly components and other molded objects from polymer resins (plastics). The pulp-based composites may be injection molded to form such objects, having sizes, shapes, surface finishes, configurations and relatively fine/small feature details, comparable to similar objects molded of plastics. Moreover, such composites may be formulated without inclusion of components derived from petroleum (such as plastics with petroleum or petroleum-derived components or precursor materials); such that the molded products are relatively rapidly dispersible when immersed in water; and such that they are biodegradable, which may contribute to making them less of a burden on water treatment and/or waste management resources. Preferably, one, more or all components of an applicator assembly as described herein will contain less than 10 percent by weight, more preferably less than 5 percent by weight, and even more preferably substantially no, petroleum, petroleum derivatives and/or plastics with petroleum or petroleum-derived components or precursor materials.

Further, materials manufactured from or containing cellulose pulp such as wood pulp may be recyclable. Applicator assemblies and components thereof as described herein may be manufactured from molding composites formulated to render the resulting molded parts recyclable in conventional paper recycling operations.

The extent of recyclability of the applicator assemblies and/or one or more of the barrel, grip and ejection plunger components as described herein may be expressed as recyclable percentage. It is believed that applicator assemblies and/or components thereof contemplated herein may be manufactured so as to exhibit recyclable percentages of at least 70 percent, more preferably at least 80 percent and even more preferably at least 90 percent; or 70 percent to 99.9 percent, more preferably 80 percent to 99.9 percent, or even more preferably from 90 percent to 99.9 percent, including all values within these ranges and any sub-ranges created thereby. It is believed that in some examples, applicator assemblies and/or components thereof contemplated herein may be manufactured to exhibit a recyclable percentage of from about 95 percent to about 99.9 percent, more preferably from about 97 percent to about 99.9 percent, or most preferably from about 98 percent to about 99.9 percent, including all values within these ranges and any sub-ranges created thereby. The recyclable percentage of the applicator assemblies of the present disclosure can be determined via test PTS-RH:021/97 (Draft October 2019) under category II, as performed by Papiertechnische Stiftung located at Pirnaer Strasse 37, 01809 Heidenau, Germany (herein, "recyclability test"). It is believed that in some examples, applicator assemblies and/or components thereof contemplated herein may be manufactured so as to exhibit an overall "pass" test outcome determined by application of the recyclability test.

Further, it is believed that applicator assemblies and/or any one, two or all of the barrel, grip and ejection plunger portions thereof contemplated herein, may be manufactured such that, when subjected to biodegradation testing under ASTM D-6691 (herein, "marine biodegradability test"), may exhibit substantial marine biodegradation within a given time period (e.g., 180 days, 200 days, 365 days, 400 days, 1 year, 2 years, 3 years, 4 years, or 5 years). It is believed that in some examples, the applicator assemblies and/or any one, two or all of the barrel, grip and ejection plunger portions thereof contemplated herein may be manufactured so as to exhibit at least 30 percent, more preferably at least 50 percent, more preferably at least 75 percent, even more preferably at least 90 percent, or most preferably substantially complete biodegradation in a marine environment within about 400 days when tested using the marine biodegradability test.

Even further, it is believed that applicator assemblies and/or any one, two or all of the barrel, grip and ejection plunger portions thereof contemplated herein, may be manufactured such that, when subjected to biodegradation testing under ASTM D-5511 (herein, "landfill biodegradability test"), may exhibit substantial landfill or composting environment biodegradation within a given time period (e.g., 180 days, 200 days, 365 days, 400 days, 1 year, 2 years, 3 years, 4 years, or 5 years). It is believed that in some examples, applicator assemblies and/or any one, two or all of the barrel, grip and ejection plunger portions thereof contemplated herein may be manufactured so as to exhibit at least 30 percent, more preferably at least 50 percent, more preferably at least 75 percent, even more preferably at least 90 percent, or most preferably substantially complete total biodegradation in a landfill environment within about 400 days when tested using the landfill biodegradability test.

Molded cellulose pulp-based products are known. Examples that may be familiar include items such as pulp-based molded egg cartons, other protective packaging/shipping trays, shells or other packaging components, food and/or beverage service trays or carriers, bowls, planting cups or pots, etc. Generally, however, while items molded from known pulp-based molding composites are often biodegradable, and in some examples may tend to lose structural integrity to some extent when moistened or saturated with water, the rate of dispersibility may not be ideal, depending upon the overall composite formulation and/or manufacturing techniques.

Molding composites that may be suitable for purposes herein, however, have now been discovered. A suitable composite may include a combination of selected cellulose pulp fibers, a selected binder material, and a selected dispersing agent. Generally, for a finished molded object, the pulp fibers impart structural robustness; the binder helps hold the fibers in place within the structure and enhances structural robustness; and the dispersing agent facilitates absorption of water into surfaces (including pore surfaces) within the structure and is water-soluble at room temperature, promoting penetration of water into the structure and dissociation of the pulp fibers, resulting in relatively rapid dispersion of the structure when immersed in water.

Following blending of the dry components in suitable proportions, a suitable quantity of water may be added to the composite to enable creation of a flowable paste or slurry that may be pumped by an extruder into an injection mold, with sufficiently low viscosity to enable filling of all cavities in the mold and yield a molded object having suitable structural integrity, a suitably smooth surface finish, and accurate formation of fine features/details reflected in the mold cavities. Preferably, the combination of selected pulp type(s), binder, dispersing agent and water content are also suitably identified and selected so as to permit removal of the water, solidification and solidification of the molded object (via application of heat and venting of water vapor) as quickly as possible, i.e., with commercially viable speed and energy usage.

It may be appreciated that, generally, increasing water content of the molding composite will make it less viscous and more flowable, but will also reduce the density of the solid materials relative the overall volume of the molded object, i.e., reduce the fraction of the volume of the mold, following injection of the composite and removal of the water (drying), that is occupied by the solid components of the composite. Reduction of density of solid components will reduce strength of the finished molded object, and may compromise the quality of the molded object in features such as surface finish and accuracy of molding of fine details. Increasing water content in the composite also will increase the time and energy required to dry and solidify the molded object.

Conversely, decreasing water content of the molding composite will make it more viscous and less flowable, and thereby increase the amount of mechanical energy required to inject the composite into the mold, and increase the risk that all cavities in the mold will not be completely filled—which may result in defects in the form of incompletely formed features. Increasing the pressure used to drive the composite into the mold may mitigate such risk. However, if the molded object is too densely occupied by solid components of the molding composite (predominately, pulp fibers and binder), it may not have sufficient porosity to permit water to penetrate into the structure with rapidity sufficient to enable dispersion in water with desired rapidity and completeness. It is believed that a level of porosity of the structure is highly desirable to facilitate penetration by water into the dry molded structure, to cause dissociation of fiber components and thereby enable dispersion thereof.

From the foregoing discussion it can be appreciated that selection and proportioning of components that will provide a molding composite that is not unacceptably time- and energy-consuming to injection-mold; does not include components derived from petroleum; and will result in an injection-molded object such as an applicator assembly component having acceptable surface finish, accurately-molded fine details, and suitable strength and structural robustness, in combination with desirably rapid dispersibility in water at room temperature, is not easily achieved. However, it is believed that the following describes a composite and process that provide a suitable balancing of these conflicting objectives.

Further, it is believed that molding composites suitable for purposes herein may be used to form molded objects adapted to have any or all characteristics deemed suitable to cause them to be flushable. It is believed that one or more of a barrel portion, a grip portion and an ejection plunger of an applicator assembly may be imparted with one or more of these characteristics, when molded of a composite as described herein. For purposes herein, the presence of flushability characteristics may be determined by applying the Flushability Guidelines, Edition Four (2018), and associated test methods, developed and published by the INDA Association of the Nonwoven Fabrics Industry.

Binder

In order to cause the wood pulp fibers to be affixed in place within the composite following drying, and impart necessary structural integrity to the molded product, it is generally desirable to include a suitable binder in the composite. Any suitable binder may be used, but for purposes herein in which human bio-compatibility, relatively rapid biodegradability, source sustainability and dispersibility are objectives, binders derived from, or having components derived from, petroleum (e.g., plastics), are not deemed desirable.

Binders that are derived from plant material may be suitable. In examples herein, plant-based starch is deemed suitable as a binder material, as it is soluble in water (upon heating and agitation thereof), has desirable properties that cause it to adhere strongly to cellulose fibers, and dries to a relatively rigid solid. It also serves enhance the ability of the solid components of the composite paste or slurry to fill mold cavities more completely.

Starch is a readily available, natural polysaccharide material that is biocompatible and relatively rapidly biodegradable, and may be combined with wood pulp fibers to serve as a binder, in a composite that may be formed into a molded object having robust strength characteristics. Starch is typically derived from plant sources. Preferably, the selected starch forms a gel upon dissolution in water, which property is believed to enhance uniform blending and suspension of fiber components, and enhance flowability, of the molding composite paste or slurry. In particular examples, corn starch and/or potato starch may be used. For purposes herein, starch may be included in the molding composite, in a weight percentage of the dry component blend (i.e., prior to addition of water to form a slurry or paste) of from about 2 percent to about 20 percent, more preferably from about 4 percent to about 15 percent, or more preferably from about 5 percent to about 10 percent, or even more preferably from about 6 percent to about 8 percent.

Dispersing Agent

Dry unmodified plant starch, however, is hydrophobic and does not dissolve in water unless the water is heated (to a temperature substantially higher than room temperature, approximately 65 degrees C.) and the starch agitated. With such energy input, the molecular components of the starch (amylose and amylopectin) dissociate from each other and form a gel, which can be blended with loose pulp fibers and suspend them in the gel to form a moldable paste or slurry. Following molding, and upon removal of the water by drying, the starch recrystallizes and forms a stable network or matrix incorporating the pulp fibers, wherein the starch acts as a cement or binder. As noted, however, the recrystallized starch does not readily dissolve in water at room temperature. As a consequence, a molded object formed of a molding composite containing only wood pulp fiber and a starch binder (with no other additives or adaptive features) may not readily disperse when immersed in water at room temperature.

It has been discovered for purposes herein, however, that addition of a suitably selected, hydrophilic dispersing agent to the molding composition can serve to promote relatively rapid absorption of water at room temperature, into an object molded of the composition, and thereby promote dissociation of pulp fibers of the composition. A dispersing agent that is not derived from petroleum is preferred, for purposes herein.

Salt of carboxymethylcellulose, in some examples sodium carboxymethylcellulose (CMC salt), has been used in the paper industry as an anti-flocculant in slurries for papermaking, promoting uniformity and smoothness of the paper product.

Prior art known to the inventors (in particular, for example, Japanese Patent Application No. 2015-253521 by Matsuzaka, hereinafter "Matsuzaka") proposes the use of CMC salt as a water soluble binder (distinguished from an anti-flocculant), in place of starch, in a moldable, cellulose pulp-based composition. Information contained in Matsuzaka suggests, that to achieve levels of dispersibility of a molded object that might be deemed sufficient for purposes contemplated herein, sodium CMC salt must be included in the molding composite blend at 25 percent to 75 percent by weight of the dry composite component blend (i.e., prior to addition of water), unless a supplement (polyvinyl alcohol—PVA) is included as a partial substitute for the CMC salt. As noted above, however, for purposes herein it is desired to avoid inclusion of components derived from petroleum (which include PVA). Information contained in Matsuzaka also suggests, by one comparative example, that inclusion of starch as a binder is counterproductive to the goal of good dispersibility of the molded object.

In contravention to the teachings of Matsuzaka, it has been discovered that, when included in a composite including particularly selected wood pulp fibers, a combination of starch and amounts of CMC salt no more than, or less than, 25 weight percent, or even no more than about 23 weight percent, or from about 15 weight percent to less than 25 weight percent, or even from 15 weight percent to 23 weight percent (weight percent of dry components of composite, prior to addition of water), can provide an effective molding composite, in which applicator assembly components molded therefrom are sufficiently mechanically robust and dispersible for purposes herein, while also exhibiting good surface finish and accuracy of molded details. Inclusion of PVA or other substitutes has been found unnecessary to mold such objects. Moreover, in contravention to the suggestion in Matsuzaka, it has been discovered that a starch binder may be included in the molding composite, while still providing a molded object in the form of an applicator assembly component, that has dispersibility in water at room temperature, suitable for purposes herein. It is believed that inclusion of a starch binder enhances strength of the molded part and accuracy of molded fine details, in comparison to omission of starch.

Without intending to be bound by theory, it is believed that material that may be obtained in the form of hydrophilic particles that attract and imbibe water upon contact and swell with absorbed water to form a gel in which suitably selected cellulose fibers may be blended, dispersed and suspended, can be particularly effective as a dispersing agent. It is believed that affinity of such particles for water, together with their swelling/gelling behavior, contributes to separation and dissociation of the cellulose fibers upon entry of water into the structure, contributing to dispersibility of an object molded from a molding composite including such dispersing agent. CMC salt exhibits such hydrophilic properties and swelling/gelling behavior. Additionally, it is acceptable for purposes herein, in that it is derived from plant sources and not from petroleum.

Cellulose Pulp

The terms "cellulose," "cellulose fibers," "cellulose pulp" and "cellulose pulp fibers," as used herein, include cellulosic fibers obtained or derived from plants, such as wood fiber, wood pulp, and other natural plant fibers, regenerated cellulose fiber such rayon, viscose or cuprammonium rayon, and high pulping yield fibers, unless specified differently. These terms also include chemically treated natural plant fibers, such as mercerized pulps, chemically stiffened or crosslinked fibers, or sulfonated fibers. Also included are mercerized natural plant fibers, regenerated natural cellulosic fibers, fibers of cellulose produced by microbes, the rayon process, cellulose dissolution and coagulation spinning processes, and other cellulosic material or cellulosic derivatives. Other cellulose fibers included are paper broke or recycled fibers and high yield fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

The term "natural plant fibers" as used herein, refers to cellulosic fibers obtained from plants, including wood fibers and wood pulp fibers such as those obtained from deciduous and coniferous trees, including softwood fibers, such as northern and southern softwood kraft fibers; and hardwood fibers, such as eucalyptus, maple, birch, and aspen; and non-wood cellulosic fibers, such as those of bamboo, cotton, abaca, kenaf, sabai grass, flax, esparto grass, straw, jute hemp, bagasse, milkweed floss, and pineapple leaf.

Cellulose pulp fibers can be prepared in high-yield or low-yield forms and can be pulped in any known method, including kraft, sulfite, high-yield pulping methods and other known pulping methods. Natural plant fibers contemplated by the present disclosure may include recycled fibers, virgin fibers or mixes thereof. Additionally, for good mechanical properties in natural plant fibers, it may be desirable that the fibers be relatively undamaged and largely unrefined or only lightly refined. The fibers can have a Canadian Standard Freeness of at least 200, more specifically at least 300, more specifically still at least 400, and most specifically at least 500.

While any fibrous plant species may serve as the source for cellulose pulp, wood pulps sourced from trees are preferred. Pulps sourced from coniferous (gymnosperm— sometimes known as softwood) trees rather than dicot (angiosperm—sometimes known as hardwood) trees are generally preferred for making cellulose pulp-based molded objects. This is because the softwood pulp fibers are relatively longer (in the range of, on average, about 2 to about 7 mm in length), and therefore, result in a relatively greater level of fiber-to-fiber entanglement within the structure. Greater fiber-to-fiber entanglement in a densely-packed arrangement (as may be imparted via injection molding) results in a structure that is relatively more mechanically robust. Some softwood tree species suitable as sources of pulp for purposes herein include spruce, pine, fir, larch and hemlock. In some examples for purposes herein white pine pulp may be preferred for its relatively high fiber strength per unit weight.

While the relatively longer fibers of softwood pulps help provide desirable mechanical strength to the finished molded object, it has been discovered that objects molded from a composite including predominately softwood pulp fibers in a densely-packed arrangement may not disperse well unless relatively greater amounts of CMC salt are included. It has been discovered, however, that substituting hardwood fibers for a substantial portion of the softwood fibers, in the overall cellulose fiber blend of the molding composite, reduces the level of need for a dispersing agent, and when starch is included as a binder, structural robustness in the molded object may be retained.

Generally, hardwood pulp fibers are shorter than softwood pulp fibers, having lengths in the range of, on average, about 0.7 mm to about 2 mm. While this feature of hardwood pulp fibers may have been believed to result in a finished molded object that may have less mechanical strength that one molded of a composite in which softwood pulp fiber is the only pulp fiber included, it has been discovered, surprisingly, that applicator assembly components molded of a composite including a substantial proportion of, or exclusively, hardwood pulp fibers, can be imparted with suitable mechanical strength and robustness, as well as enhanced dispersibility, when combined with a suitable binder and a suitable dispersing agent.

Without intending to be bound by theory, it is believed that the smaller size of hardwood fibers reduces the level of fiber-to-fiber entanglement within the molded object, making dissociation and dispersion (upon immersion in water) relatively more rapid. At the same time, it is believed that inclusion of starch as a binder mitigates, to some extent, the loss of mechanical robustness of the molded object that would otherwise be attributable to replacement of longer softwood pulp fibers by shorter hardwood pulp fibers, in the molding composite.

For the foregoing reasons it may be desired to include a substantial proportion of hardwood pulp fibers in the molding composite. In some examples it may be desired that the hardwood pulp fibers include one or more of eucalyptus, aspen, poplar, maple, birch, beech, ash and birch pulp fibers (including species that are genetically modified for, e.g., increased growth rate). In some examples, aspen, eucalyptus or birch fibers (or any blend or combination thereof) may be preferred for desirable fiber size and density characteristics, more preferably eucalyptus or birch, and most preferably eucalyptus.

For a good balance of mechanical strength, surface finish, and accuracy of the molded object, combined with good dispersibility, the dry weight ratio of hardwood pulp fibers to softwood pulp fibers may be selected to be at least 1:2, or at least 1:1 (equal parts), or at least 2:1, or at least 3:1 or even substantially 1:0 (substantially all hardwood pulp fibers). Without intending to be bound by theory, it is believed that when mechanical strength is a greater priority, the selected ratio may be closer to 1:1; and when maximized dispersibility is a greater priority, the selected ration may be closer to substantially 1:0.

For the appropriate level of mechanical strength and porosity of the molded structure (explained below), it is believed that the cellulose fibers in the molding composite should constitute 55 percent to 85 percent, more preferably 60 percent to 80 percent, and still more preferably 65 percent to 75 percent, by weight of the combined dry components of the molding composite (i.e., prior to addition of water).

Other

Lubricating Agent

In some circumstances it may be desirable to include a lubricating agent in the molding composite, for one or more of the following purposes: (1) improving the kneadability, extrudability, flowability and/or moldability of the molding composite via means other than adding more water (i.e., reducing the energy input required to create a uniform, homogeneous blend of the component materials; and reducing the energy input required to drive the blended composite through and/or into an extruder and/or sprues, runners, gates and molds in a molding system, without increasing energy and/or time needed to remove water from the composite following molding); and (2) following molding, improving the releasability of the molded object from the mold (i.e., reducing chances that the molded object will stick to the mold and potentially be cracked or otherwise damaged as a result, or leave residue in the mold, upon removal of the molded object from the mold).

The lubricating agent may include a long-chain fatty acid salt of a non-alkali metal, including a non-polar part from a fatty acid chain and a polar part of the non-alkali metal. The agent, desirably, is water-insoluble; exhibits hydrophobicity and activates surfaces; and has characteristics of a lubricant either in a liquid state or in powder form. These qualities enable the agent to act as an internal lubricant between/among the other particulate components of the blend when it is kneaded; may serve to prevent the molding composite from adhering to surfaces of sprues, runners, gates and molds; and can generally reduce energy input needed for processing. Without intending to be bound by theory, it is also believed that such a lubricating agent may contribute to porosity and/or help provide pathways by which water vapor can escape the molded object, as water is driven out by application of heat energy following molding. This may help reduce time and/or energy input required to solidify and dry the molded object, following molding.

Examples of suitable long-chain fatty acid salts of non-alkali metals include, but are not limited to: calcium stearate, magnesium stearate, zinc stearate, calcium laurate, magnesium laurate, zinc laurate, aluminum laurate, strontium laurate, aluminum stearate, and strontium stearate. One of these may be included in the component blend, or any blend any two or more of these may be included.

If it is determined that inclusion of a lubricating agent is desired under the circumstances, lubricating agent may be included in a quantity amounting to, preferably, from 0.3 to 2.0 weight percent of the total dry component blend. A quantity that amounts to less than 0.3 weight percent of the total dry component blend may not be sufficient because the desired effects described above may not be satisfactorily achieved. Conversely, a quantity of the lubricating agent amounting to more than 2.0 weight percent of the total dry component blend may be found excessive because it may be counterproductive to quickly achieving a homogeneous blend (some internal friction between the surfaces of the particulate components may be desirable to retain effects of shear forces that contribute to rapid blending). Further, when discrete flows of molding composite join within various shaped spaces defined by a mold, an excessive quantity of lubricating agent may prevent the discrete flows from completely fusing and/or forming a strong interface. Similarly, an excessive quantity of lubricating agent may compromise the ability of two or more dried, completed molded objects (such as separately molded parts of a whole) to be bonded or fused together via reapplication of water to mating surfaces of the parts to be joined, as described herein.

Pigment

It has been found that the molding composite described herein, products molded therefrom, may be relatively unaffected in quality, by addition of limited quantities of pigment material, provided that the pigment material selected is not chemically reactive with water or any of the other components of the molding composite under the molding conditions referenced herein. Accordingly, the composite described herein enables the manufacturer to mold parts in a large variety of colors. In order to avoid substantial effect on the moldability of the composite, it is believed that pigment, if desired, should be included to a maximum of 5 percent, more preferably 4 percent, and still more preferably 3 percent, by weight of the dry component blend.

Water

Water is added to the dry wood pulp, binder and dispersant component blend during blending and/or kneading and heating in standard mixing equipment, used to transform the dry components into an injectable and moldable paste or slurry. The quantity of water added may be varied to achieve an optimized balance of viscosity (for ease and accuracy of complete molding and molding of fine features), porosity of the finished molded object, and minimization of the quantity of water included, that must be removed during the drying process following injection (in the interest of minimization of energy and time required for drying). From experimentation it is believed that molded applicator assembly components having the desirable properties discussed herein may be successfully injection molded by preparation of a dry component blend having cellulose fiber, binder and dispersing agent components as identified herein, in weight proportions set forth herein, which is then mixed with water, heated and kneaded to prepare a flowable slurry or paste. The volume ratio of dry component blend to water may be from 55:45 to 75:25, and may be adjusted according to the desired dry component composition selected for optimized viscosity and water content for molding and molded object porosity.

In other examples, dry/precursor components of the molding composite may be dispersed in a relatively high water content slurry, as disclosed in, by way of non-limiting example, PCT App. No. WO 2020/016416. In such examples, a method of producing an applicator assembly or component thereof may include applying the slurry to a porous forming face of a first mold in a first forming step to form a layer of pulp deposit thereagainst, pressing the layer against the porous forming face of the first mold, while heating the layer and drawing a vacuum through the porous forming face of the first mold; then in a second step transferring the layer to a porous forming face of a second mold, and pressing the layer against the porous forming face of the second mold, while heating the layer and drawing a vacuum through the porous forming face of the second mold. The method of molding from a molding composites at high water content in a slurry may be as described in above-cited WO 2020/016416, which is incorporated herein by reference in its entirety.

Adjustment for Porosity

It is believed that adjusting the amount of water added to the composite (as well as adjustment of the other components of the composite within ranges discussed above) so as to result in a density/porosity of the finished, dried molded object within the ranges discussed below will yield a molded object having a balance of (1) structural strength; (2) surface smoothness; (3) accuracy of molded fine details; and (4) dispersibility upon immersion in water at room temperature, suitable for purposes herein. Further, without intending to be bound by theory, it is believed that it may be important to control and provide a certain level of porosity of the molded object.

Generally, porosity as measured herein is a characterization of the pore structure with a dried, finished molded object. Some level of porosity is desired so that water may penetrate and move with suitable rapidity throughout the structure of the molded object, to cause the fibers to dissociate, enhancing dispersibility. Regardless of the selections and proportions of the fiber, binder and dispersing agent components of the molding composite, if the molded object is not sufficiently porous it will not permit entry of water into its structure with rapidity required for suitably rapid dispersion.

On the other hand, an overly porous structure (in part characterized by relatively low solid component density and relatively high void percent fraction of the overall volume occupied by the molded object) may exhibit a desirable level of dispersibility, but have insufficient structural robustness (mechanical strength) or accuracy of molded fine details suitable for purposes herein. Accordingly, the objective is to strike a suitable balance.

From experimentation with molding of blends of molding composite components, it is believed that an applicator assembly component molded of a cellulose pulp-based molding composite should have a level of porosity characterized by a dry void space fraction of from 6 percent to 40 percent, more preferably 10 percent to 35 percent, and still more preferably 12 percent to 30 percent. Generally, dry void space fraction of a molded object approximates the fraction of the overall volume defined by the outer/exposed surfaces of the dry molded object (those surfaces that were in direct contact with the mold surfaces during molding), that is devoid of solid material (dried cellulose fiber, binder and/or dispersing agent).

Additionally, it may be advantageous to ensure that the dry void space fraction is distributed through the structure of the molded object in pores of suitable sizes (manifest in a mean void thickness within a prescribed range). Without intending to be bound by theory, it is believed that relatively smaller pores (characterized by relatively small mean void thickness) are advantageous because they are more uniformly distributed and thereby provide for more even penetration of water into the structure of the molded object upon immersion. On the other hand, if the pores are too small, desirably rapid penetration of water into the structure may be prevented. Without intending to be bound by theory, it is believed that pore size for a particular molding composite and particular molded object may be controlled by regulating the level of mixing and kneading applied to the composite upon addition of water, and prior to extrusion, as well as by controlling the rapidity of injection and filling of the mold, and of drying/solidification of the molded object, which may be affected by the injection pressure applied to fill the mold. For molded objects of the type contemplated herein, it is believed that, in combination with the dry void space fraction ranges set forth above, mean void thickness is, ideally, 50 µm to 300 µm, more preferably 60 µm to 200 µm, and even more preferably 70 µm to 150 µm.

For purposes herein, the dry void space fraction and mean void thickness of pores within the structure of a molded object are measured using the Dry Porosity Scanning Method described below.

Process

Preparation of Molding Composite

In some examples, the dry components may be provided in some examples, in the form of pre-formed pellets, having the desired ratios of the respective components, uniformly blended. Otherwise, the respective components desired may be obtained, measured and blended to the desired proportions at the time of manufacture of the molded objects.

Preparation of Molding Composite Paste or Slurry

The composite pellets or dry component blend may be blended with water and supplied to a screw-type extrusion apparatus similar to those used to extrude/mold plastics in conventional injection molding processes. Heat energy may be supplied to, or via, the extrusion apparatus, to heat the mixture to promote dissolution and gelling of the binder component (starch) in the added water, promoting a uniform distribution of the starch component molecules, dispersing agent particles and wood throughout the resulting paste or slurry, providing a consistent, uniform blend.

Extrusion and Molding

After the composite with added water is heated and kneaded by the extruder and transformed into a paste or slurry with suitable viscosity for molding, it may be driven under pressure through a system of sprues, runners and gates into one or more molds configured to define the features desired in the finished molded product.

The foregoing sentence generally describes a process known as "injection molding." However, unless otherwise specified the terms "mold," "molding" and "molded" are not necessarily limited to injection molding, but encompass other types and methods of molding, including any process in which a composite in a liquid, fluid, plastic or plastically deformable state is formed and subsequently solidified, hardened or otherwise finished into a solid object having a suitably stable finished form, using one or more mold components reflecting the desired shape, size and features of the object, with or without application of heat. Thus, for purposes herein, these terms include but are not necessarily limited to injection molding, casting, press-molding, compression-molding, rotational molding and stamping.

Subparts

In some examples, the molds may be configured to define parts or subparts, e.g., halves, of the complete finished molded product. Referring to FIGS. 5, 6A, 6B, 7A and 7B, for example, in an applicator assembly it may be desired to mold only the grip portion 25 using the composite described herein, while the barrel portion 21 may be formed of another material such as rolled paper, e.g., as used for conventional paper tube applicator assemblies. Following the manufacture of these respective applicator components, the grip portion 25 may be joined to the barrel portion by any suitable mechanism, such via mechanically mating geometry, as suggested in FIG. 5. In one example, grip portion 25 may be molded with a cylindrical fitting portion 40 sized to concentrically and snugly fit within the rearward end of a barrel portion 21 formed of a hollow substantially cylindrical paper tube. The two components may be affixed together via use of a suitable glue or adhesive (preferably water soluble). Alternatively, or in addition thereto, fitting portion 40 may be molded with friction-increasing features, for example, one or more circumferential ribs 41, configured to grip the cylindrical inner surface 21a of barrel portion 21 and thereby cause grip portion 25 to be effectively secured within/to barrel portion 21 without need for glue or adhesive. As suggested by the figures, such ribs 41 may be chamfered to enable fitting portion 40 to interact with interior surface 21a of barrel portion 21, in a manner that enables fitting portion 40 be more easily inserted into rearward end of barrel portion 21, while more effectively resisting withdrawal/separation of the two components.

Molding a part such as grip portion 25 in two or more subparts such as halves 25a and 25b may simplify the molding process by reducing the number of features and complexity of each individual molded subpart—facilitating injection of the composite into the molds and improving accuracy of reproduction of the molded feature details defined by the molds. Further, reducing the size and volume of the molded parts by dividing them into subparts facilitates faster removal of water from the molded composite, via heating of the molds and venting of steam. In the example depicted in FIGS. 6A, 6B, 7A and 7B, grip portion 25 may be molded in two subparts, e.g., halves 25a and 25b. Following molding, the subparts 25a and 25b may be joined together along mating surfaces 45a, 45b, via any suitable mechanism, e.g., glue or adhesive (preferable water soluble), forming seam 45 in finished molded grip portion 25.

It has been discovered, surprisingly, that two parts molded of a composite as described herein, following molding, solidification and drying thereof, may be re-wetted with controlled, limited quantities of water along surfaces that are intended to be joined, and thereafter joined along those surfaces, by merely bringing them into contact under light pressure, without need for use or inclusion of added glues or adhesives, or more complex processes. Without intending to be bound by theory, it is believed that objects molded of particular composites as described herein readily admit water into their outer surfaces and begin to dissociate, and thereby re-assume a paste or slurry form to limited and controllable depths along the wetted surfaces, and thereby become tacky. This feature of the composite can be used to effectively fuse or weld the subparts along the wetted surfaces, forming a surprisingly strong joint or seam along the joined surfaces following re-drying. It is believed that the same features of the composites described herein that promote dissociation and dispersion upon full immersion in water, enable such joining of molded subparts via more limited wetting. Thus, for example, an applicator assembly component, or any part thereof, may have subparts thereof molded in, e.g., two or more molds, and the subparts may be joined to form the complete component or part thereof merely by wetting respective mating surfaces of the subparts along the intended location(s) of the joints/seams. Additionally, objects molded of composites described herein can be joined with other objects formed of cellulose-based components (such as objects formed of cardboard or paperboard), such that a unitary product may be manufactured having one or more parts molded of composites as described herein, and one or more parts formed of other cellulose-based components. In a particular example of an applicator assembly component depicted in FIGS. 5 through 7B, a grip portion 25 may be molded of a molding composite as described herein, and joined to a substantially cylindrical and/or tubular hollow barrel portion 21 formed of paperboard. The grip portion 25 may be molded in parts such as halves 25a and 25b, and then joined to form a seam 45 as described above. Subsequently, a fitting portion 40 may be joined with the barrel portion 21 by insertion thereinto. In connection with this process, the fitting portion 40 may be wetted to a limited extent as suggested above, to facilitate and/or effect bonding between the fitting portion 40 and the inner surface 21a of the barrel portion 21.

Figure 5:
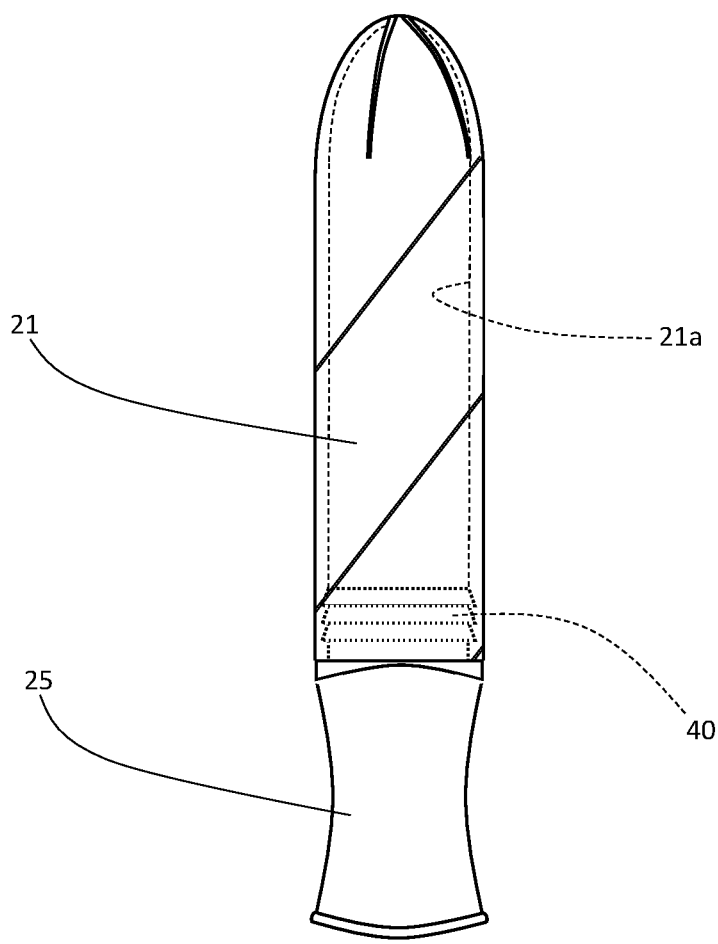
FIG. 5 is a longitudinal side view of barrel and grip portions of an applicator assembly.
Figure 6A:
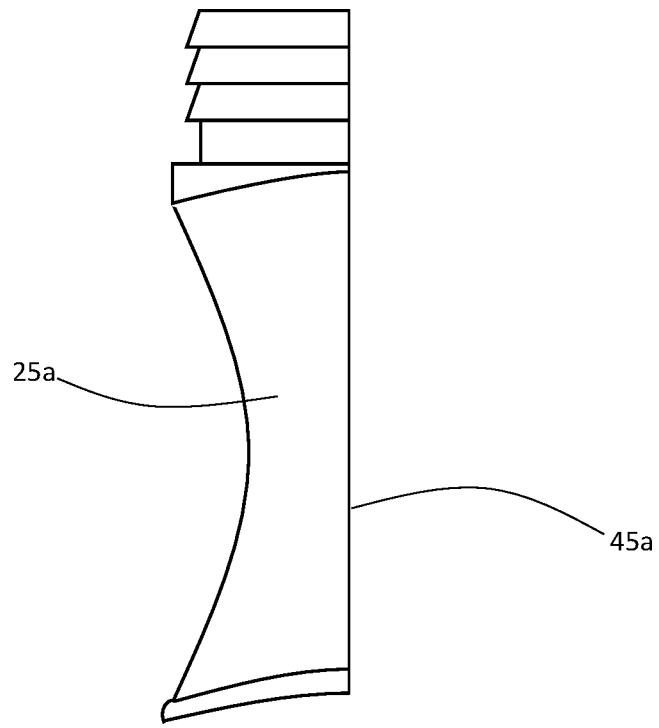
FIGS. 6A and 6B are longitudinal side views of respective molded subparts of a grip portion of an applicator assembly.
Figure 6B:
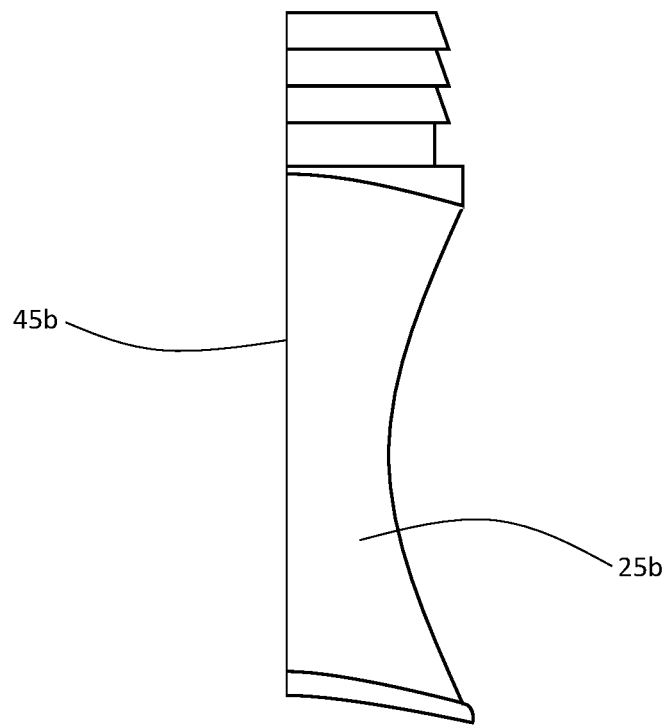
Figure 7A:
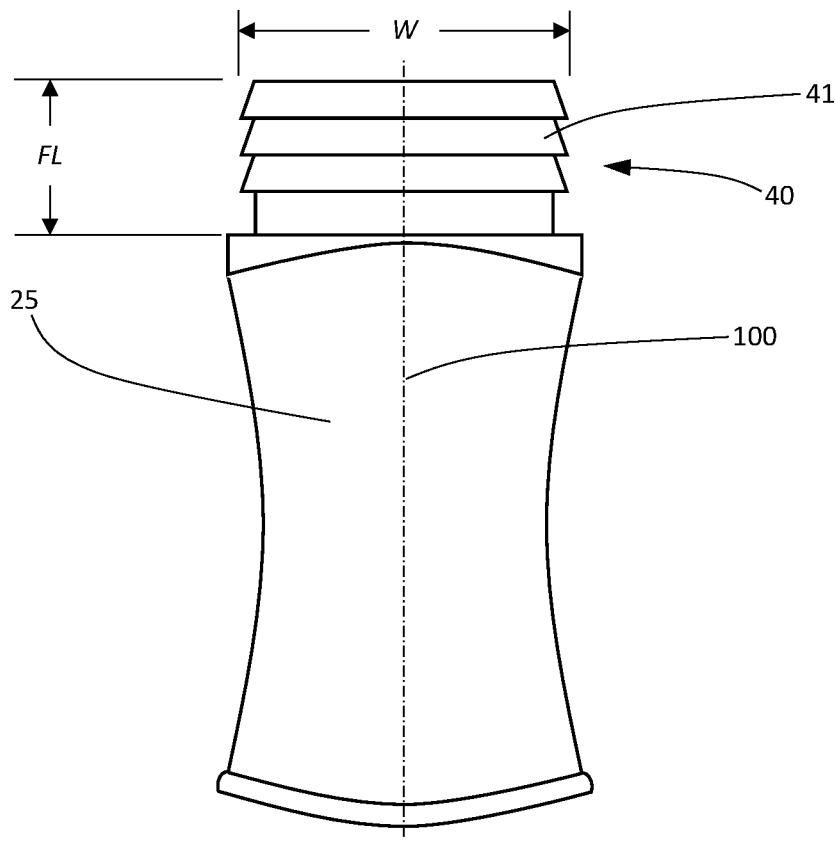
FIGS. 7A and 7B are longitudinal side views of a grip portion, in first and second rotational orientations, the second orientation being rotated 90 degrees from the first orientation, about a longitudinal axis of an applicator assembly.
Figure 7B:
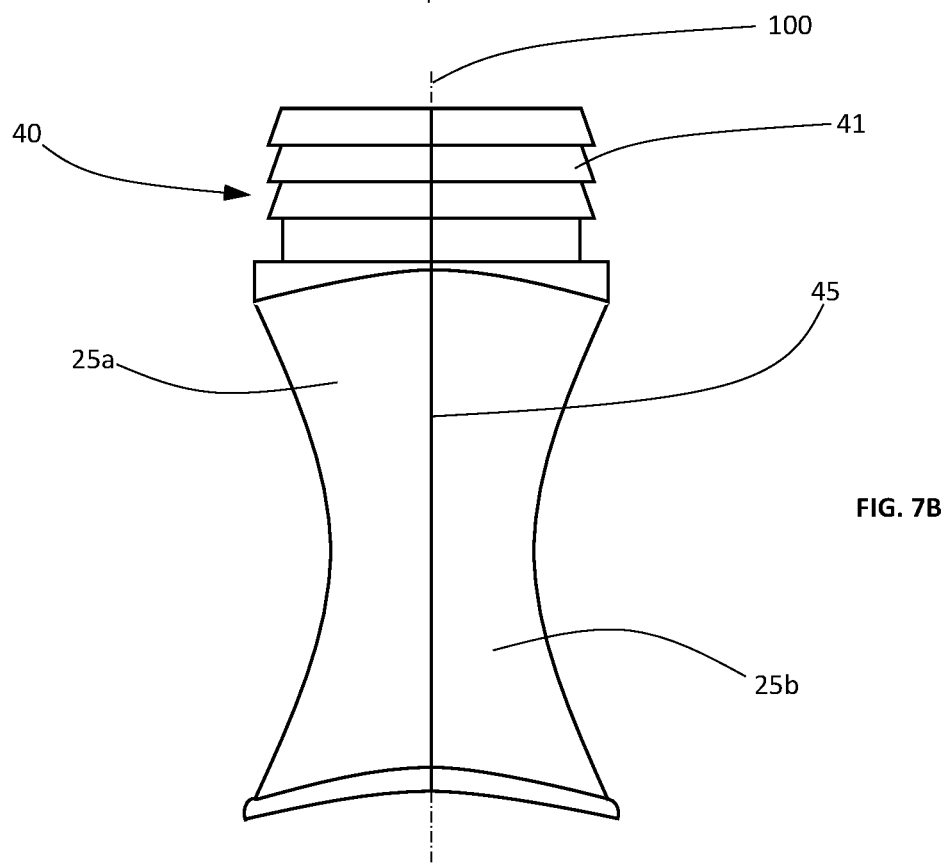

Now referring to FIGS. 5 and 7A, where it is desired to manufacture an applicator assembly from separately-formed gripping 25 and barrel 21 portions as described above, it may be desired also to ensure that fitting portion 40 of grip portion 25 is appropriately sized to minimize chances of separation and/or failure at the junction therebetween from lateral bending stress, such as might be applied inadvertently or intentionally during transport, handling or use of the applicator by a user. Accordingly, it may be desired that fitting portion 40 have a length FL that is equal to, or preferably greater than, one-half (i.e., 0.5) width W, where length FL is the total length of the portion (e.g., fitting portion 40) that is inserted into the barrel portion 25; and width W is the largest lateral dimension of the fitting portion inserted. (It will be observed that, when fitting portion 40 has a largest lateral cross section that is circular, width W will be equal to the diameter of that cross section.)

Water Removal

During, or following, injection of the molding composite into a mold, the mold may be heated to cause the water in the composite to evaporate out, causing the composite to solidify in the molded shape. The mold may be vented in any suitable manner to allow the resulting water vapor (steam) to escape. In some examples of processes, the mold may be opened very slightly to vent steam, and then reclosed to resume heating as well as ensure accuracy of the molded part as the composite solidifies. The mold may be opened slightly and reclosed as many times as may be needed to vent steam, until the water content of the molded part is reduced to the desired level for a finished molded part, typically less than 13 percent, less than 11 percent, or even less than 5 percent, by weight of the molded part, or from 5 percent to 13 percent by weight of the molded part. Retention of a limited quantity of water within the structure within these ranges is believed to enable the molded part to better maintain the dimensions and shape of the mold and/or desired finished shape and dimensions. For purposes herein, a molded object having a water content of 13 percent or less by weight is deemed "dry".

Dry Porosity Scanning Method

There micro-CT measurement method described below is used to measure dry void space fraction and mean void thickness of a tampon applicator component molded of a pulp-based composite. The measurements are based on analysis of a 3D x-ray sample-images obtained on a micro-CT instrument capable of acquiring a dataset at high isotropic spatial resolution. A suitable instrument is the Scanco µCT 50 available from Scanco Medical AG, Brüttisellen, Switzerland, or equivalent. The instrument is interfaced with a dedicated computer running software to control the image acquisition and reconstruction of the raw data into a 3D image. The 3D image is then analyzed using image analysis software (suitable image analysis software are MATLAB available from The Mathworks, Inc., Natick, Massachusetts, and Avizo Lite available from Visualization Sciences Group/FEI Company, Burlington, Massachusetts, or equivalents).

Sample Preparation:

Obtain a test sample from the tampon applicator assembly of interest as follows. The complete tampon product including tampon and applicator assembly is removed from any outer packaging material. The tampon is ejected from the applicator assembly and discarded. The test sample is the entire component of the applicator assembly, of interest because it is molded of a pulp-based composite. The test sample is to be left in its original configuration, e.g., if the sample is cylindrical with a hollow interior region, no attempt is made to cut, flatten or otherwise deform it.

Condition the test sample at 23 degrees C.±2 degrees C. and 50%±2 percent relative humidity for 4 hours prior to testing.

Image Acquisition:

The micro-CT instrument is set up and calibrated according to the manufacturer's specifications. The sample is placed inside a 19 mm diameter holder (as supplied with the equipment), using two rings fabricated of low density material to snugly hold the sample, center it within the holder and prevent its movement within/relative the holder during the scan. The low density material may be any material having differentiably lower density than the material of the test sample, e.g., styrofoam. The sample is placed such that its longitudinal axis is upright and vertical to the scanner detector. A single 3D dataset of contiguous 7 µm (microns) isotropic voxels is collected. Images are acquired with the source at 45 kVp and 177 µA with no additional low energy filter with a 25 mm field of view. These current and voltage settings may be optimized to produce the maximum contrast in the projection data with sufficient x-ray penetration through the sample, but once optimized held constant for all substantially similar samples. A total of 2000 projection images are obtained with an integration time of 525 ms, 3 averages for a single batch and a voxel size of 7 µm (microns) per pixel. A sufficient number of interconnected overlapping batches were collected to image the complete volume of the sample, and the batches subsequently stitched together. The projection images are reconstructed into a 3D dataset of a sufficient number of cross-sections having an isotropic spatial resolution of 7 μm (microns) and saved in 16-bit RAW format to preserve the full detector output signal for analysis, where grey levels reflect changes in x-ray attenuation, which in turn relates to material density.

Image Processing:

The 3D dataset is loaded into the image analysis software and trimmed (cropped) to remove the surrounding holder and excess background space, thus creating a 3D clean volume of interest for data processing and analysis. Trimming is performed such that the maximum amount of the sample in the analysis window is retained in the 3D image, and the empty background space surrounding the sample is minimized. This trimmed 3D image is scaled from 16-bit to 8-bit, and thresholded using Otsu's method, which calculates the threshold level that minimizes the weighted intraclass variance, to separate and remove the background signal due to air, but maintain the signal from the solid portion within the sample image. The solid portions containing non-zero voxels are referred to as "solid voxels." Voids within the solid portions of the sample are referred to as "void voxels" and assigned a value of 0.

A connected components algorithm is executed on the trimmed 3D image, which identifies and groups together any solid voxels that are 26-connected (touching faces, edges, or corners) to any neighboring solid voxels. Any solid voxel clusters containing fewer than 1000 connected voxels are identified as noise, removed from the 3D image and assigned void voxel values.

The total void volume (sum of all void voxel volumes) and total solid volume (sum of all solid voxel volumes) occupied within the sample structure in the 3D image are used to calculate the percent dry void space fraction and dry solid space fraction. To determine the total volume occupied by the sample, a morphological closing operation was used to generate an outer surface that completely enclosed the sample structure, and to remove the inner void or hollow space within the geometry of the sample. The closing operation was accomplished via a 3 by 3 by 3 cube structuring element implementing dilation followed by erosion operations on the solid fraction of the sample. A minimum number of dilations followed by an equivalent number of erosions was used to enclose the sample allowing the total volume occupied by the sample structure in the 3D image to be determined. Divide the total void volume by the total volume of the sample structure, multiply by 100 and report as dry void space fraction to the nearest 0.1%. Now subtract the percent dry void space fraction from 100 and report as dry solid space fraction to the nearest 0.1%.

To characterize the localized size distribution of the void and solid portions of the sample, a sphere fitting algorithm is implemented. To analyze the void space, the sphere fitting method starts by generating a Euclidean Distance Map (EDM), which assigns grey level values equal to the distance each void voxel is from its nearest solid voxel boundary. Based on the EDM data, the 3D void space representing pores is tessellated with spheres sized to match the EDM values. Voxels enclosed within larger spheres are assigned the radius value of the largest sphere in which they are enclosed. In other words, each void voxel is assigned the radius value of the largest sphere that both fits within the void space boundary and includes the assigned voxel. This allows a volume weighted average of the spheres to be calculated by taking the average of the assigned individual void voxel radii values. The average of all the individual void voxel radii values is calculated, then multiplied by two and reported as the mean void thickness to the nearest 0.01 micron. In like fashion, the same sphere fitting algorithm is implemented on the solid portion of the sample. The average of all the assigned individual solid voxel radii values is calculated, then multiplied by two and reported as mean solid thickness to the nearest 0.01 micron.

In view of the foregoing disclosure, the following non-limiting examples are contemplated:

1. An applicator assembly comprising a barrel portion, a grip portion and an ejection plunger configured to slide coaxially within one or both the barrel portion and the grip portion, wherein one or more of the barrel portion, grip portion and ejection plunger is/are molded from a molding composite comprising cellulose fibers.
2. The applicator assembly of example 1 wherein one of said molded one or more of the barrel portion, grip portion and ejection plunger is porous.
3. The applicator assembly of example 2 wherein said porous one of the molded one or more of the barrel portion, grip portion and ejection plunger has a dry void space fraction from 6 percent to 40 percent, more preferably 10 percent to 35 percent, and still more preferably 12 percent to 30 percent.
4. The applicator assembly of either of examples 2 or 3 wherein said porous one of the molded one or more of the barrel portion, grip portion and ejection plunger has a mean void thickness of 50 μm to 300 μm, more preferably 60 μm to 200 μm, and even more preferably 70 μm to 150 μm.
5. The applicator assembly of any of the preceding examples wherein the cellulose fibers comprise one or both of hardwood pulp fibers and softwood pulp fibers.
6. The applicator assembly of example 5 wherein a dry weight ratio of hardwood pulp fibers to softwood pulp fibers is at least 1:2, or at least 1:1, or at least 2:1, or at least 3:1 or even substantially 1:0.
7. The applicator assembly of either of examples 5 or 6 wherein the softwood fibers are selected from the group consisting of spruce fibers, pine fibers, fir fibers, larch fibers, hemlock fibers and white pine fibers, and combinations thereof, and preferably white pine fibers.
8. The applicator assembly of any of examples 5-7 wherein the hardwood fibers are selected from the group consisting of eucalyptus fibers, aspen fibers, poplar fibers, maple fibers, birch fibers, beech fibers and ash fibers, and combinations thereof, and preferably aspen fibers.
9. The applicator assembly of any of the preceding examples wherein the molding composite comprises a binder.
10. The applicator assembly of example 9 wherein the binder comprises a polysaccharide.
11. The applicator assembly of example 10 wherein the polysaccharide is derived from plant matter.
12. The applicator assembly of either of examples 10 or 11 wherein the polysaccharide comprises a starch.
13. The applicator assembly of example 12 wherein the starch constitutes from about 2 percent to about 20 percent, more preferably from about 4 percent to about 15 percent, or more preferably from about 5 percent to about 10 percent, or even more preferably from about 6 percent to about 8 percent, by weight of the molding composite, excluding water content.

14. The applicator assembly of any of the preceding examples wherein the molding composite comprises a dispersing agent.
15. The applicator assembly of example 14 wherein the dispersing agent comprises particles that are hydrophilic and form a gel upon contact with water.
16. The applicator assembly of either of examples 14 or 15 wherein the dispersing agent comprises carboxymethylcellulose (CMC).
17. The applicator assembly of example 16 wherein the dispersing agent comprises CMC salt, preferably substantially entirely CMC salt.
18. The applicator assembly of any of examples 14-17 wherein the dispersing agent constitutes no more than, or preferably less than, 25 weight percent, more preferably no more than 23 weight percent, or from 15 weight percent to less than 25 weight percent, or even from 15 weight percent to 23 weight percent of the molding composite, excluding water content.
19. The applicator assembly of any of the preceding examples wherein the cellulose fibers constitute 55 percent to 85 percent, more preferably 60 percent to 80 percent, and still more preferably 65 percent to 75 percent, by weight of the molding composite, excluding water content.
20. The applicator assembly of any of the preceding examples wherein the molding composite comprises a lubricating agent.
21. The applicator assembly of example 20 wherein the lubricating agent comprises a long-chain fatty acid salt of a non-alkali metal.
22. The applicator assembly of either of examples 20 or 21 wherein the lubricating agent comprises a compound selected from the group consisting of calcium stearate, magnesium stearate, zinc stearate, calcium laurate, magnesium laurate, zinc laurate, aluminum laurate, strontium laurate, aluminum stearate, strontium stearate and combinations thereof.
23. The applicator assembly of any of examples 20-22 wherein the lubricating agent is included in an amount from 0.3 to 2.0 percent, by weight of the molding composite, excluding water content.
24. The applicator assembly of any of the preceding examples wherein the one or more of the barrel portion, grip portion and ejection plunger molded from the molding composite has a water content of no greater than 13 weight percent, or from 5 to 13 weight percent.
25. The applicator assembly of any of the preceding examples wherein one or more of the barrel portion, grip portion and ejection plunger is flushable.
26. The applicator assembly of any of the preceding examples wherein one or both the barrel portion and the grip portion is/are molded from the molding composite.
27. The applicator assembly of example 26 wherein the one or both the molded portion(s) is/are molded in at least two separately molded subparts that have been joined together following molding.
28. The applicator assembly of example 27, wherein the subparts that have been joined together have been joined without application of any substantial quantity of added glue or adhesive material.
29. The applicator assembly of any of examples 26-28 wherein the grip portion is molded from the molding composite.
30. The applicator assembly of example 29 wherein the barrel portion comprises a length of tube formed of paper, and is joined to the grip portion.
31. The applicator assembly of any of the preceding examples wherein one, two or all of the barrel portion, grip portion and ejection plunger contain(s) less than 10 percent by weight, more preferably less than 5 percent by weight, and even more preferably substantially no, petroleum, petroleum derivatives and/or plastics with petroleum or petroleum-derived components or precursor materials.
32. The applicator assembly of any of the preceding examples wherein one, two or all of the barrel portion, grip portion and ejection plunger is/are recyclable.
33. The applicator assembly of example 32 wherein one, two or all of the barrel portion, grip portion and ejection plunger exhibit(s) a recyclable percentage of at least 70 percent, more preferably at least 80 percent, and even more preferably at least 90 percent in application of the recyclability test cited herein.
34. The applicator assembly of any of the preceding examples wherein one, two or all of the barrel portion, grip portion and ejection plunger exhibits a "pass" test outcome in application of the recyclability test cited herein.
35. The applicator assembly of any of the preceding examples wherein one, two or all of the barrel portion, grip portion and ejection plunger exhibit(s) at least 30 percent, more preferably at least 50 percent, more preferably at least 75 percent, even more preferably at least 90 percent, or most preferably substantially complete biodegradation in a marine environment within about 400 days when tested using the marine biodegradability test.
36. The applicator assembly of any of the preceding examples wherein one, two or all of the barrel portion, grip portion and ejection plunger exhibit(s) at least 30 percent, more preferably at least 50 percent, more preferably at least 75 percent, even more preferably at least 90 percent, or most preferably substantially complete biodegradation in a marine environment within about 400 days when tested using the landfill biodegradability test.
37. A tampon product comprising a compressed absorbent tampon housed within the applicator assembly of any of the preceding examples.
38. A pessary product comprising a pessary housed within the applicator assembly of any of examples 1-36.
39. A menstrual cup product comprising a menstrual cup housed within the applicator assembly of any of examples 1-36.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" where a small deviation would be functionally equivalent.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon applicator assembly comprising a barrel portion, a grip portion and an ejection plunger configured to slide coaxially within one or both the barrel portion and the grip portion,
    wherein one or both of the barrel portion and grip portion is/are molded from a molding composite comprising cellulose fibers, and
    wherein the molded one or both of the barrel portion and the grip portion have a mean void thickness of 50 μm to 300 μm.

2. The applicator assembly of claim 1 wherein said one or both of the molded barrel portion and/or grip portion has a dry void space fraction from 6 percent to 40 percent.

3. The applicator assembly of claim 1 wherein the cellulose fibers comprise hardwood pulp fibers and softwood pulp fibers in a dry weight ratio of hardwood pulp fibers to softwood pulp fibers of 1:2 to 3:1.

4. The applicator assembly of claim 3 wherein the softwood fibers are selected from the group consisting of spruce fibers, pine fibers, fir fibers, larch fibers, hemlock fibers and white pine fibers, and combinations thereof.

5. The applicator assembly of claim 3 wherein the hardwood fibers are selected from the group consisting of *eucalyptus* fibers, aspen fibers, poplar fibers, maple fibers, birch fibers, beech fibers and ash fibers, and combinations thereof.

6. The applicator assembly of claim 1 wherein the molding composite comprises a binder, the binder comprising a polysaccharide derived from plant matter.

7. The applicator assembly of claim 6 wherein the polysaccharide comprises a starch, the starch constituting from about 2 percent to about 20 percent of the weight of the molding composite, excluding water content.

8. The applicator assembly of any of the preceding claims wherein the molding composite comprises a dispersing agent, the dispersing agent comprising particles that are hydrophilic and form a gel upon contact with water.

9. The applicator assembly of claim 8 wherein the dispersing agent comprises CMC salt, and wherein the dispersing agent constituting from 15 weight percent to 23 weight percent of the molding composite.

10. The applicator assembly of claim 1 wherein the cellulose fibers constitute 55 percent to 85 percent of the weight of the molding composite, excluding water content.

11. The applicator assembly of claim 1 wherein the molding composite comprises a lubricating agent comprising a compound selected from the group consisting of calcium stearate, magnesium stearate, zinc stearate, calcium laurate, magnesium laurate, zinc laurate, aluminum laurate, strontium laurate, aluminum stearate, strontium stearate and combinations thereof.

12. The applicator assembly of claim 11 wherein the lubricating agent is included in an amount from 0.3 to 2.0 percent, by weight of the molding composite, excluding water content.

13. The applicator assembly of claim 1 wherein the one or both of the barrel portion and/or grip portion has/have a water content of 5 to 13 weight percent.

14. The applicator assembly of claim 1 wherein the one or both the molded portion(s) is/are molded in at least two separately molded subparts that have been joined together following molding, wherein the subparts that have been joined together have been joined without application of any substantial quantity of added glue or adhesive material.

15. The applicator assembly of claim 1 wherein the grip portion is molded from the molding composite.

16. The applicator assembly of claim 15 wherein the barrel portion comprises a length of tube formed of paper, and is joined to the grip portion.

17. The applicator assembly of claim 1 wherein one, two or all of the barrel portion, grip portion and ejection plunger contain(s) less than 10 percent by weight petroleum, petroleum derivatives and/or plastics with petroleum or petroleum-derived components or precursor materials.

18. The applicator assembly of claim 1 wherein one, two or all of the barrel portion, grip portion and ejection plunger is/are recyclable and exhibit(s) a recyclable percentage of at least 70 percent in application of the recyclability test cited herein.

19. The applicator assembly of claim 1 wherein one, two or all of the barrel portion, grip portion and ejection plunger exhibit(s) at least 75 percent biodegradation in a marine environment within about 400 days when tested using the marine biodegradability test, and/or, exhibit(s) at least 75 percent biodegradation in a landfill environment within about 400 days when tested using the landfill biodegradability test.

20. A tampon applicator assembly comprising a barrel portion, a grip portion and an ejection plunger configured to slide coaxially within one or both the barrel portion and the grip portion,
    wherein at least one of the barrel portion, the grip portion, and the ejection plunger is molded from a molding composite comprising cellulose fibers, and
    wherein the molded at least one of the barrel portion, the grip portion, and the ejection plunger have a mean void thickness of 50 μm to 300 μm and a dry void space fraction from about 6 percent to about 40 percent.

* * * * *